United States Patent
Yamauchi et al.

(10) Patent No.: US 7,208,523 B2
(45) Date of Patent: Apr. 24, 2007

(54) ALANINE- AND GLYCINE-CONTAINING THERAPEUTIC AGENT FOR HEPATITIS

(75) Inventors: Masayoshi Yamauchi, Yokohama (JP); Ichiro Sonaka, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 337 days.

(21) Appl. No.: 10/196,816

(22) Filed: Jul. 18, 2002

(65) Prior Publication Data

US 2002/0198262 A1   Dec. 26, 2002

Related U.S. Application Data

(63) Continuation of application No. PCT/JP01/00109, filed on Jan. 12, 2001.

(30) Foreign Application Priority Data

Jan. 18, 2000  (JP) ............................. 2000-008658
Mar. 6, 2000   (JP) ............................. 2000-060097

(51) Int. Cl.
*A01N 37/12*   (2006.01)
*A01N 37/44*   (2006.01)
*A61K 31/195*  (2006.01)
*A61K 39/29*   (2006.01)

(52) U.S. Cl. .................... 514/561; 424/225.1; 514/894
(58) Field of Classification Search ........ 424/400–401, 424/225.1; 514/2, 561, 894
See application file for complete search history.

(56) References Cited

U.S. PATENT DOCUMENTS

| 4,085,207 | A | * | 4/1978  | Aoki et al. ................... 514/23 |
| 4,491,589 | A | * | 1/1985  | Dell et al. ................... 514/400 |
| 4,499,076 | A |   | 2/1985  | Ohashi et al. |
| 4,698,419 | A |   | 10/1987 | Chazov et al. |
| 5,580,903 | A |   | 12/1996 | Mawatari et al. |
| 6,048,543 | A | * | 4/2000  | Schneider et al. .......... 424/442 |

FOREIGN PATENT DOCUMENTS

| DE | 26 36 828 | 2/1978 |
| JP | 5-221 858 | 8/1993 |
| JP | 6-183962  | 7/1994 |

OTHER PUBLICATIONS

Pharmacotherapy, A Pathophysiologic Approach, 2nd ed. Elsevier, Dipiro et al. p. 579, figure 34.1, 1992.*
M. Yin, et al., The Journal of Pharmacology and Experimental Therapeutics, vol. 286, No. 2, XP-002281490, pp. 1014-1019, "Glycine Accelerates Recovery From Alcohol-Induced Liver Injury[1]", Aug. 1998.

* cited by examiner

*Primary Examiner*—Sreeni Padmanabhan
*Assistant Examiner*—Yong S. Chong
(74) *Attorney, Agent, or Firm*—Oblon, Spivak, McClelland, Maier & Neustadt, P.C.

(57) ABSTRACT

The therapeutic agent for hepatitis, containing alanine and glycine, has only a slight toxicity and it can be administered either orally or intravenously to improve the liver function.

12 Claims, 2 Drawing Sheets

\* $p<0.05$ vs galactosamine
\# $p<0.05$ vs glycine a : p<0.025 vs. Gal
b : p<0.001 vs. Gly
c : p<0.001 vs. Ala

ALANINE- AND GLYCINE-CONTAINING THERAPEUTIC AGENT FOR HEPATITIS

BACKGROUND OF THE INVENTION

The present invention relates to a therapeutic agent for hepatitis such as acute or chronic viral hepatitis, acute or chronic alcoholic hepatitis, acute or chronic drug-induced hepatitis, or fulminant hepatitis.

Hepatitis is caused by hepatitis viruses of A, B or C type, or by the intake of a large amount of a drug or by the long term intake of a drug. It is known that, in patients suffering from hepatitis, the liver function is seriously lowered by the lowering of the function of liver mitochondria or by the necrosis of liver cells. Particularly in cases of acute hepatitis or fulminant hepatitis, plasma transaminase is distinctively increased by the necrosis of liver cells in a wide range.

For the treatment of such liver disorders, interferon therapy as a kind of antiviral therapies is employed. However, no direct effect of interferon can be recognized on the improvement of the function of mitochondria or on the regeneration of the liver. Further, it is said that although glutathione, Tathion injection (Yamanouchi Pharmaceutical Co., Ltd.) and Neo-Minophagen C, Strong (Minophagen Co. Ltd) generally used for the treatment of hepatitis are effective in improving the plasma transaminase value, their effects in improving the function of liver mitochondria and in regenerating the liver are yet poor. In addition, because those drugs are in the form of injections, it is expected to have the development of a drug which can be orally administered.

Various therapeutic agents for hepatitis have been developed under these circumstances. For example, Japanese Patent Unexamined Published Application (hereinafter referred to as "J. P. KOKAI") No. Sho 63-54320 discloses that alanine and glutamine have an antialcoholismic effect; J. P. KOKAI No. Hei 5-213746 discloses that alanine has the antialcoholismic effect; J. P. KOKAI No. Hei 5-221858 discloses a therapeutic agent for hepatitis, characterized by containing at least one of alanine, glutamine and ornithine; and J. P. KOKAI No. Hei 5-229940 discloses that alanine and/or glutamine accelerates the liver regeneration. J. P. KOKAI No. Sho 62-164619 discloses that a combination of predetermined amounts of cysteine and/or cysteine dimer with alanine, aspartic acid or glycine exhibits an effect of improving the substance synthesis function of the liver; J. P. KOKAI No. Hei 6-183962 discloses that at least one of glycine, serine and alanine prevents an injury of kidneys, liver, spleen, intestines, pancreas and other parenchymatous organs and the skin caused by the anoxia; and WO 96/25861 discloses that at least one of glycine, serine and alanine has an effect of lowering TNF level and is effective in preventing and treating alcohol-induced hepatopathy and also disorder in the intestines and pancreas.

On the other hand, the inventors reported that the oral administration of glycine or alanine alone inhibits a hepatopathy caused by the intraabdominal administration of galactosamine [The 85th Congress of Japanese Society of Gastroenterology (1999)]. Further, it was recently reported that the effect of glycine for controlling the hepatopathy caused by galactosamine would be mainly obtained by the control of TNF α secretion from Kupffer cells [Hepatology (1999) 29: 737–745].

DISCLOSURE OF THE INVENTION

The object of the present invention is to provide a therapeutic agent for hepatitis, which has only a slight toxicity and which can be administered either orally or intravenously to improve the liver function.

The present invention was completed on the basis of a finding that when a combination of alanine and glycine is used for hepatopathy caused by galactosamine, with HepG2 cells, a therapeutic effect for the hepatitis more excellent than that obtained by using alanine or glycine alone can be obtained.

Namely, the present invention provides a therapeutic agent for hepatitis, which contains alanine and glycine.

BEST MODE FOR CARRYING OUT THE INVENTION

Although the therapeutic agent of the present invention for hepatitis can contain alanine and glycine in an unlimited ratio, the mass ratio of alanine to glycine is preferably 100/1 to 1/100, more preferably 10/1 to 1/10, and most preferably 7/3 to 3/7. The molar ratio of them is preferably about 1/1.

As for the medicinal forms of the therapeutic agent of the present invention for hepatitis, they can be, for example, a powder, granules, tablets, sugar-coated tablets, capsules and liquid for the oral administration; and a suspension, detergent, emulsion, ampoule and injection for the parenteral administration; or a combination of them. When the therapeutic agent is in the form of the injection, it may be an amino acid transfusion or a preparation containing both alanine and glycine so far as the ratio of the sum of them to the total amino acids is at least 20% or so far as the dose of these amino acid is at least 10 g/day.

When the therapeutic agent of the present invention is used as a food, it may be in the form of a powder, sugar-coated tablets, capsules, liquid or the like.

The dose can be easily determined depending on the symptoms of the patients. Alanine and glycine are given in an amount of at least 1 g in total a day for adults. Because both alanine and glycine are approved as foods, it is unlikely that they have toxicity, particularly acute toxicity.

The therapeutic agent of the present invention for hepatitis is effective in treating acute or chronic, viral, alcoholic or drug-induced hepatitis, or fulminant hepatitis.

The following Examples will further illustrate the present invention.

EXAMPLE 1

Figure 1:
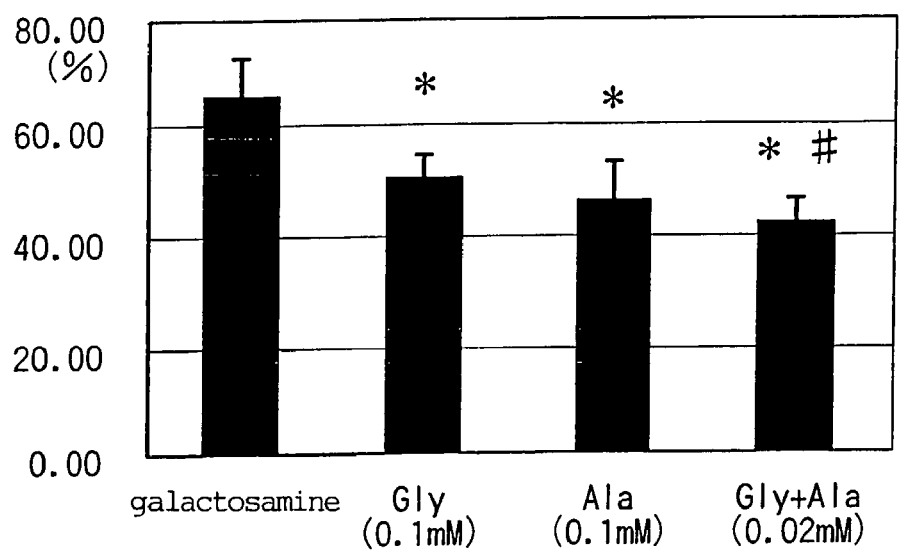
FIG. 1 shows the comparison of the effect obtained by administering glycine and alanine separately from each other and the effect obtained by administering the combination of glycine and alanine in Example 1.

The concentration of HepG2 cells was controlled at $3 \times 10^5$/ml. 200 μl of the cells were cultured in αMEM and FBS on a 96-well microplate for 24 hours. Then 25 mM of D-galactosamine was added to only the sample in αMEM to cause liver a cell disorder. 0.1 mM of glycine or alanine, or 0.02 mM of glycine+alanine (each 0.01 mM of glycine and alanine) was added to the sample thus obtained. 24 hours after the addition, the cytotoxicity (%) was determined on the basis of LDH activity in the supernatant liquid. FIG. 1 shows the cell-protecting effect obtained by adding both 0.01 mM of glycine and 0.01 mM of alanine as compared with that obtained by adding 0.1 mM of either glycine or alanine. In the table, the values are average±SD and n=5 to 6.

It is apparent from the results in FIG. 1 that as compared with the cytotoxicity observed after the addition of either glycine or alanine, the cytotoxicity observed after the addition of the combination of glycine and alanine in a concentration of 1/10 is far lower. This fact shows the effect obtained by the combination.

EXAMPLE 2

Figure 2:
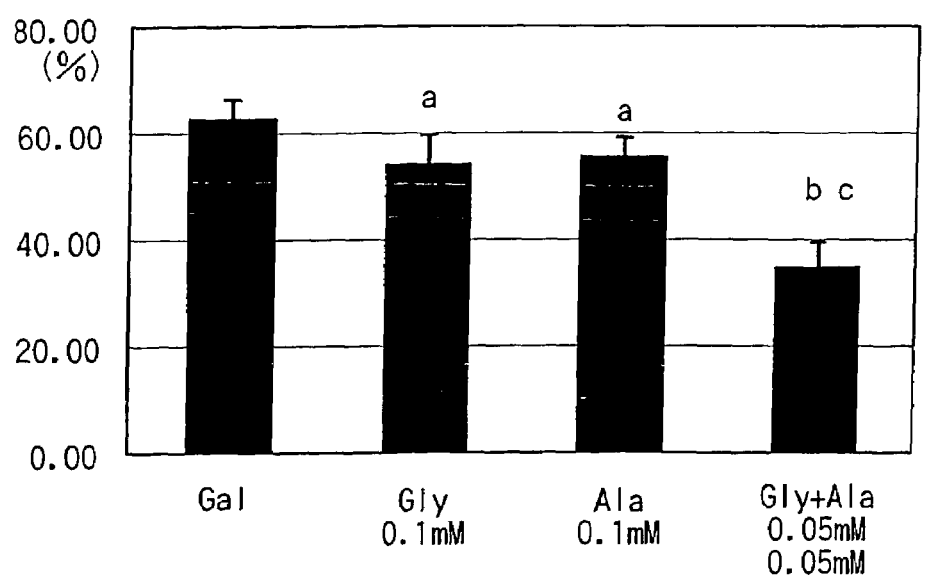
FIG. 2 shows the comparison of the effect obtained by administering glycine and alanine separately from each other and the effect obtained by administering the combination of glycine and alanine in Example 2.

The cytotoxicity (%) was determined in the same manner as that of Example 1 except that 0.1 mM of glycine or alanine was added or 0.1 mM of the combination of glycine+alanine (0.05 mM of glycine and 0.05 mM of alanine) was added. FIG. 2 shows the cell-protecting effect obtained by adding both 0.05 mM of glycine and 0.05 mM of alanine as compared with that obtained by adding 0.1 mM of either glycine or alanine. In the table, n is 6.

It is apparent from the results shown in FIG. 2 that as compared with the cytotoxicity observed after the addition of either glycine or alanine, the cytotoxicity observed after the addition of the combination of alanine and glycine is synergistically lower.

What is claimed is:

1. A method of treating a patient suffering from hepatitis, which comprises administering to said patient in need thereof a therapeutic composition consisting essentially of alanine and glycine.

2. The method of claim 1, wherein a mass ratio of alanine to glycine is 100/1 to 1/100.

3. The method of claim 1, wherein a mass ratio of alanine to glycine is 10/1 to 1/10.

4. The method of claim 1, wherein a mass ratio of alanine to glycine is 7/3 to 3/7.

5. The method of claim 1, wherein a molar ratio of alanine to glycine is about 1.

6. The method of claim 1, wherein the therapeutic composition is orally administered to said patient.

7. The method of claim 1, wherein the therapeutic composition is parenterally administered to said patient.

8. The method of claim 6, wherein the therapeutic composition is in a form selected from the group consisting of a powder, a granule, a tablet, a sugar-coated tablet, a capsule and a liquid.

9. The method of claim 7, wherein the therapeutic composition is in a form selected from the group consisting of a suspension, a detergent, an emulsion, an ampoule and an injection.

10. The method of claim 9, wherein the therapeutic composition is in an injection form.

11. The method of claim 1, wherein alanine and glycine are given in an amount of at least 1 g in total a day for adults.

12. The method of claim 1, wherein said patient suffering from hepatitis is suffering from a form of hepatits selected from the group consisting of acute hepatitis, chronic hepatitis, viral hepatitis, alcoholic-induced hepatitis, drug-induced hepatitis, and fulminant hepatitis.

* * * * *